United States Patent [19]
Baker et al.

[11] Patent Number: 5,188,756
[45] Date of Patent: Feb. 23, 1993

[54] TOPICAL CLEANSING AND CONDITIONING COMPOSITION

[75] Inventors: Christopher G. Baker, Port Jervis, N.Y.; Elliott S. Zucker, Shohola, Pa.

[73] Assignee: Kolmar Laboratories, Inc., Port Jervis, N.Y.

[21] Appl. No.: 741,554

[22] Filed: Aug. 7, 1991

[51] Int. Cl.$^5$ .............................................. C11D 3/08
[52] U.S. Cl. ......................... 252/174.15; 252/174.21; 252/544; 252/547; 252/548; 252/551
[58] Field of Search ...................... 252/174.15, 174.21, 252/544, 547, 548, 551

[56] References Cited
U.S. PATENT DOCUMENTS 4,338,211  7/1982  Stiros ..................................... 252/548

Primary Examiner—Patrick P. Garvin
Assistant Examiner—Brent M. Peebles
Attorney, Agent, or Firm—Andrus, Sceales, Starke & Sawall

[57] ABSTRACT

A cleansing and conditioning composition for topical application comprising the combination of a surfactant, an emollient, a cationic material, a film former, a polyamino sugar condensate and water. The interaction of the ingredients effects both cleansing and moisturization of the skin.

8 Claims, No Drawings

TOPICAL CLEANSING AND CONDITIONING COMPOSITION

BACKGROUND OF THE INVENTION

Traditionally, the cleansing and moisturizing regimen for the skin consists of a three-step process, comprising cleansing, toning and moisturizing. Each step requires a specific product, i.e. a cleanser, toner and moisturizer, and each requires a particular method of use.

Cleansers are designed to remove dirt, cosmetics, and the normal skin byproducts, such as sebum, dead skin cells, and the like. However, cleansers tend to leave residual materials on the skin, such as soap film and oily components.

Toners are designed to remove the soap residue and other potential pore clogging materials, while moisturizers serve to mimic the action of normal skin secretions in maintaining suppleness in the skin and provide a barrier to evaporation. The use of the moisturizer is necessitated by the removal of natural skin secretions by the cleanser and toner.

The use of the conventional cleansing-toning-moisturizing system requires the consumer to maintain stocks of three different products, learn the appropriate regimen for use of each individual product of the system and take the time to follow each specific regimen in its appropriate order.

Recently, there has been a desire for more convenience in personal care products which has been evidenced by increased sales of conditioning shampoos, breath freshening toothpastes, and other multi-functional products. The use of a single product which provides a multiple function saves the consumer both time and effort and possibly money.

SUMMARY OF THE INVENTION

The invention is directed to a multiple function cleansing conditioner for topical application, which comprises a water base containing a surfactant, an emollient, a cationic material, a film former, and a polyamino sugar condensate.

The surfactant is a cosmetically acceptable low irritancy-type which reduced surface tension on the skin, thus allowing dirt and oils to be washed away with water.

The emollient can take the form of oils, fatty acids, or fatty acid esters.

The cationic material, such as oleyl palmityl palmitoleyl keratin hydroxypropyl dimonium chloride lactate has a net positive charge and is attracted to human skin which carries a net negative charge, thus providing a smooth silky feel to the skin.

The film former, which can take the form of a silicone based wax, or a high molecular weight silicone polymer, produces a coating which remains on the skin after rinsing and thus aids in maintaining the polyamino sugar condensate, which is a skin moisturizer, on the skin.

The unique interaction of the cationic material, the film former, and the polyamino sugar condensate in a gentle surfactant base, provides both a cleansing and conditioning action for the skin.

Through use of the invention the consumer can maintain a stock of only a single product which will provide the multiple function of cleansing and conditioning. The use of a single product will require only one regimen of treatment or application.

Other objects and advantages will appear in the course of the following description.

DESCRIPTION OF THE PREFERRED EMBODIMENT

The invention is directed to a cosmetic composition which incorporates both cleansing and conditioning action. In general, the composition has the following formulation in weight percent:

| | |
|---|---|
| 10% to 40% | Surfactant |
| 1% to 15% | Emollient |
| 0.5% to 5.0% | Cationic material |
| 0.5% to 2.5% | Film former |
| 0.05% to 1.0% | Polyamino sugar condensate |
| Balance | Water |

The preferred composition is as follows:

| | |
|---|---|
| 15% to 35% | Surfactant |
| 2% to 10% | Emollient |
| 0.8% to 2.0% | Cationic material |
| 0.5 to 1.5% | Film former |
| 0.10% to 1.50% | Polyamino sugar condensate |
| Balance | Water |

The surfactant is water soluble and is a type commonly used in cosmetic products, having low irritancy to the skin. Examples of surfactants which can be used in the composition are alkyl ether sulfates, such as sodium laureth sulfate; glycerides such as PEG-6 caprylic/capric glycerides; betaines such as cocamidopropyl betaine; ethoxylates such as PEG-10 soya sterol; amides such as cocamide DEA, myristamide DEA, or PEG-20 methyl glucose ether disteartate; and ethers such as Oleth-10 (sold by Croda, Inc.).

The emollients to be used in the composition are cosmetically acceptable types and can take the form of oils, such as olive oil, castor oil, mineral oil, silicone oil, such as cyclomethicone; fatty acid esters, such cetearyl palmitate or isopropyl-12-hydroxystearate, or mixed fatty alcohols, such as cetearyl alcohol.

The cationic materials provide substantivity to the skin, which in turn produces a smooth silky feel. Human skin tends to carry a negative charge and the positively charged cationic material is attracted to the skin and will remain in contact with the skin surface for a prolonged period of time. The cationic material preferably contains fatty acid moieties, i.e. oleic, linoleic, etc., which are known to be naturally present in the skin, and can also include keratin, lactic acid, amino acid, or phospholipid moieties. Specific examples of the cationic material which can be used are oleyl palmityl palmitoleyl, keratin hydroxypropyl dimonium chloride lactate, wheatgerm-amidopropyl dimethylamine hydrolyzed wheat protein, and guar hydroxypropyl trimonium chloride.

The polyamino sugar condensate is a skin moisturizing material and is the CTFA approved name for Aqualizer EJ sold by Kolmar Laboratories, Inc. Port Jervis, NJ.

The film formers produce a coating which remains on the skin after rinsing and the coating or film aids in maintaining the conditioning agents on the skin. The film formers also protect the skin from environmental conditions and aid in the retention of natural moisture within the skin. Specific examples of film formers that can be used are silicon based waxes, such as stearoxytrimethylsilane and stearyl alcohol; silicon polymers, such as dimethiconol; and cationic cellulose derivatives such as polyquaternium 4.

In addition to the above-mentioned ingredients, the composition can also contain from 5% to 15% by weight of botanical or plant extracts, such as lavender, rosemary, witch hazel, mimosa bark, and chamomile.

A small amount, up to an amount of 0.5% by weight of a material, such a tocopheral linoleate, can also be included which serves to enhance the moisturizing effect of the polyamino sugar condensate.

Also, small amounts up to 0.5% by weight of materials such as fragrances, preservatives, and colorants can be included in the composition.

Specific examples of the composition of the invention are as follows:

EXAMPLE NO. 1

| Material | Percent |
| --- | --- |
| Water | QS to 100 |
| Polyquaternium | 0.20 |
| Sodium laureth sulfate | 15.00 |
| Lauramidopropyl betaine | 5.00 |
| Lauramide DEA | 2.00 |
| Oleth 20 | 0.50 |
| Polyamino sugar condensate | 0.20 |
| Rosemary extract | 4.00 |
| Mallow extract | 3.00 |
| Stearoxytrimethyl silane | 0.05 |
| PEG-6 Caprylic/Capric Glyceride | 0.50 |
| Stearic acid | 1.00 |
| Cetearyl alcohol | 0.20 |
| PEG-10 soya sterol | 0.20 |
| Cetyl alcohol | 0.10 |
| Ceteareth-20 | 0.10 |
| Isopropyl-12-Hydroxystearate | 0.10 |
| Oleyl palmityl palmitoleyl keratin hydroxypropyl dimonium chloride lactate | 0.50 |
| Cyclomethicone | 0.08 |
| Dimethiconol | 0.02 |
| Colorants | QS |
| Preservatives | 0.60 |
| Fragrance | 0.20 |

EXAMPLE NO. 2

| Material | Quantity |
| --- | --- |
| Water | QS to 100 |
| Ammonium laureth sulfate | 20.00 |
| Polyquaternium 4 | 1.00 |
| Cocamidopropyl betaine | 5.00 |
| Cocamide DEA | 2.00 |
| PPG-20 methyl glucose ether distearate | 0.20 |
| Polyamino sugar condensate | 0.20 |
| Witch hazel extract | 5.00 |
| Lavender extract | 2.00 |
| Stearoxytrimethyl silane | 0.10 |
| PEG-3 castor oil | 0.50 |
| Stearic acid | 1.00 |
| Cetearyl alcohol | 0.20 |
| PEG-10 soya sterol | 0.20 |
| Cetyl alcohol | 0.10 |
| Olive oil | 0.30 |
| Ceteareth-20 | 0.10 |
| Isopropyl-12-hydroxystearate | 0.10 |
| Oleyl palmityl palmitoleyl keratin hydroxypropyl dimonium chloride lactate | 1.50 |
| Cyclomethicone | 0.05 |
| Dimethiconol | 0.05 |
| Colorants | QS |
| Preservatives | 0.60 |
| Fragrance | 0.20 |

EXAMPLE NO. 3

| Material | Percent |
| --- | --- |
| Water | QS to 100 |
| Guar hydroxypropyl trimonium chloride | 0.10 |
| Sodium myreth sulfate | 10.00 |
| Myristamidopropyl betaine | 10.00 |
| Myristamide DEA | 5.00 |
| Oleth 20 | 0.50 |
| Polyamino sugar condensate | 0.20 |
| Chamomile Extract | 6.00 |
| Mimosa bark extract | 3.00 |
| Stearoxytrimethyl silane | 0.05 |
| PEG-6 Caprylic/capric glycerides | 0.50 |
| Myristic acid | 1.00 |
| Cetearyl alcohol | 0.20 |
| PEG-20 Castor oil | 0.20 |
| Cetyl alcohol | 0.10 |
| Ceteareth-20 | 0.10 |
| Isopropyl-12-hydroxystearate | 0.10 |
| Wheatgerm-amidopropyl dimethyl-amine hydrolyzed wheat protein | 0.40 |
| Tocopherol Linoleate | 0.10 |
| Cyclomethicone | 0.08 |
| Dimethiconol | 0.02 |
| Colorants | QS |
| Preservatives | 0.60 |
| Fragrances | 0.20 |

The combination of ingredients used in the composition of the invention provides a unique interaction which both effectively cleanses the skin and provides a moisturizing benefit for the skin. Thus, the multiple functions which heretofore had been available only through use of multiple products are achieved through the use of a single product.

Various modes of carrying out the invention are contemplated as being within the scope of the following claims particularly pointing out and distinctly claiming the subject matter which is regarded as the invention.

We claim:

1. A cleansing and condition composition for topical application, comprising by weight from 10% to 40% of a low irritancy cosmetically acceptable surfactant, 1% to 15% of an emollient, 0.5% to 5.0% of a cationic material having a net positive charge and selected from the group consisting of oleyl palmityl palmitoleyl keratin hydroxypropyl dimonium chloride lactate, wheatgerm-amidopropyl dimethylamine hydrolyzed wheat protein, guar hydroxypropyl trimonium chloride, and mixtures thereof, 0.5% to 2.5% of a cosmetically acceptable film former, 0.05% to 1.00% of polyamino sugar condensate, and the balance water.

2. The composition of claim 1, wherein said surfactant is present in an amount of 15% to 35% by weight, said emollient is present in an amount of 2% to 10% by weight, said cationic material is present in an amount of 0.8% to 2.0% by weight, said film former is present in the amount of 0.5% to 1.5% by weight and said polyamino sugar condensate is present in an amount of 0.10 to 0.5% by weight.

3. The composition of claim 1, and including from 5% to 15% by weight of a cosmetically acceptable plant extract.

4. The composition of claim 1, wherein said surfactant is selected from the group consisting of alkyl ether sulfates, betaines, ethoxylates, amides, and ethers.

5. The composition of claim 1, wherein said film former is selected from the group consisting of silicon based waxes, silicon polymers, polyquaternium 4 and mixtures thereof.

6. The composition of claim 1, wherein said emollient is selected from the group consisting of oils, fatty acids, fatty acid esters, and mixtures thereof.

7. The compositions of claim 3, wherein said plant is selected from the group consisting of lavender, rosemary, witch hazel, mimosa bark, chamomile, and mixtures thereof.

8. The composition of claim 1, and further including up to 0.5% by weight of tocopheral linoleate.

* * * * *